United States Patent [19]

Yamada et al.

[11] Patent Number: 4,591,421
[45] Date of Patent: May 27, 1986

[54] AIR/FUEL RATIO DETECTOR

[75] Inventors: Tetsusyo Yamada; Shintaro Hirate, both of Aichi, Japan

[73] Assignee: NGK Spark Plug Co., Ltd., Aichi, Japan

[21] Appl. No.: 681,336

[22] Filed: Dec. 13, 1984

[30] Foreign Application Priority Data

Dec. 15, 1983 [JP] Japan ................... 58-237623

[51] Int. Cl.$^4$ ............................................. G01N 27/58
[52] U.S. Cl. ...................... 204/406; 204/410; 204/412; 204/425; 204/426; 204/427
[58] Field of Search ............... 204/412, 410, 424, 425, 204/426, 427, 428, 429, 1 S, 406; 60/276; 123/489

[56] References Cited

U.S. PATENT DOCUMENTS 4,158,166 6/1979 Isenberg .................. 204/426 X
4,450,065 5/1984 Yamada et al. ................ 204/412

Primary Examiner—G. L. Kaplan
Attorney, Agent, or Firm—Sughrue, Mion, Zinn, Macpeak & Seas

[57] ABSTRACT

An A/F (Air Fuel) ratio detector providing precise control of the operating A/F ratio of an internal combustion engine whether the engine is operating in the fuel-rich or fuel-lean region or at the theoretical (stoichiometric) point. The detector includes both a pump element and a sensor element, each composed of an oxygen-ion-conductive solid electrolyte having formed on both sides thereof a porous electrode. The pump and sensor elements are disposed facing one another with a small gap therebetween. A wall is disposed parallel to the sensor element on the side opposite the gap and is sealed to the solid electrolyte of the sensor element except at a base portion, thereby defining an air compartment open to the atmosphere. An electric current is passed through the pump element, and the resulting potential produced across the sensor element is taken as an indication of the operating A/F ratio.

15 Claims, 7 Drawing Figures

AIR/FUEL RATIO DETECTOR

BACKGROUND OF THE INVENTION

The present invention relates to an A/F (Air/Fuel) ratio detector for use in the measurement or control of the concentration of oxygen in exhaust gas from a burning device such as an internal combustion engine or gas burner.

An oxygen sensor composed of an ion-conductive solid electrolyte (e.g., stabilized zirconia electrolyte) coated with porous electrode layers (e.g., Pt porous layers) is capable of detecting the concentration of oxygen near a theoretical (stoichiometric) A/F ratio of exhaust gas from an internal combustion engine to thereby detect the combustion efficiency of the engine. Detection is carried out by sensing a change in an electromotive force that is produced by the difference between the partial oxygen pressure of the exhaust gas and that of atmospheric air. This type of oxygen sensor is presently used in numerous applications, for example, in an automobile for the purpose of controlling its internal combustion engine to run at the theoretical air/fuel ratio.

The conventional oxygen sensor exhibits a large amount of change in output if the operating A/F ratio (which is the weight ratio of air to fuel) is near the theoretical value of 14.7, but otherwise the resulting change in output is negligibly small. Therefore, the output from this sensor cannot be effectively used for an engine operating at an A/F ratio other than near the theoretical value.

Japanese Published Unexamined Patent Application No. 153155/1983 shows an oxygen concentration detector composed of a pair of oxygen-ion-conductive solid electrolyte plates each having an electrode layer on both sides in a selected area close to one end thereof. The two plates are fixed parallel to each other and spaced to provide a gap in an area corresponding to that selected area having the electrode layers. One electrolyte plate with electrode layers is used as an oxygen pump element, and the other plate also having electrode layers is used as an electrochemical cell sensor element that operates in response to the difference in oxygen concentration between the ambient atmosphere and the gap between the two plates. This type of detector has a quick response and a decreased temperature dependency, but according to experiments conducted by the present inventors, the output of the sensor is ambiguous. That is, when this device is operated in a fuel-rich region having an A/F ratio lower than the theoretical value of 14.7, the direction of change of the output away from the theoretical value is the same as that for operation in the fuel-lean region. Because of the existence of two possible A/F ratios for a single output, the sensor can be used only when it is definitely known whether the burning device to be controlled is operating in the fuel-rich or fuel-lean region.

It has also been found that the detector shown in Japanese Published Unexamined Patent Application No. 153155/1983 has considerable difficulty in achieving precise or quick detection or measurement of the theoretical A/F ratio or near-theoretical values.

SUMMARY OF THE INVENTION

Accordingly, an object of the present invention is to provide an A/F ratio detector that is capable of accurately and quickly detecting the operating A/F ratio of a burner such as an internal combustion engine whether it is operating in the fuel-rich region, fuel-lean region or at the theoretical A/F ratio.

Another object of the present invention is to provide an A/F ratio detector that enables precise and simple feedback control over the A/F ratio for the full dynamic range of the engine.

The above and other objects of the present invention are met by an A/F ratio detector comprising a solid electrolyte oxygen pump element and a solid-electrolyte oxygen-concentration-difference-actuated electrochemical cell sensor element, each element being in the form of an oxygen-ion-conductive solid electrolyte having a porous electrode formed on both sides, the electrochemical cell sensor element being disposed to face the pump element with a small gap therebetween, an air compartment open to the atmosphere being formed on the side of at least the sensor element opposite the small gap, and means for passing an electric current through the pump element, the resulting output from the sensor element providing an output signal for detecting the actual air/fuel ratio.

With this arrangement, the detector of the present invention has the advantage of enabling accurate and quick detection of the A/F ratio for all or part of the operating range including both the fuel-rich and fuel-lean regions. Furthermore, the detector has a long service life as it requires only a small pump current (i.e., low current density on the electrode surface) for producing a given output signal.

DESCRIPTION OF THE PREFERRED EMBODIMENTS

A preferred embodiment of an A/F ratio detector of the present invention will hereunder be described with reference to the accompanying drawings.

Figure 1:
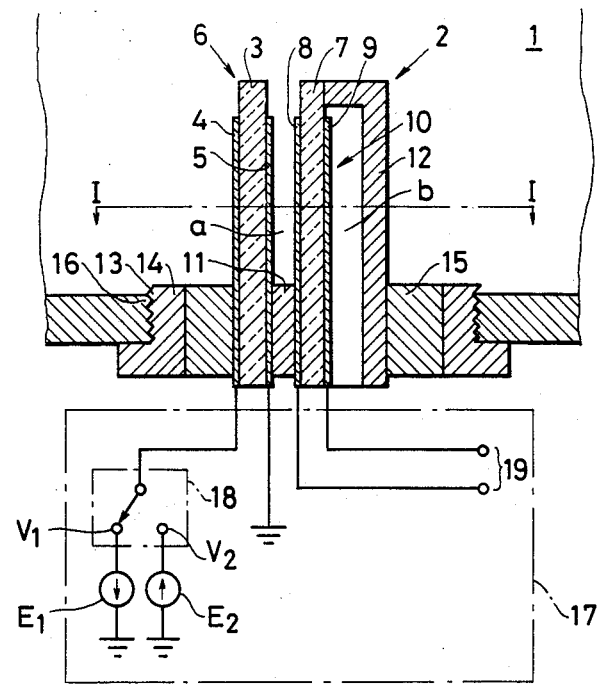
FIG. 1 shows, in cross section, an A/F ratio detector according to one embodiment of the present invention.
Figure 2:
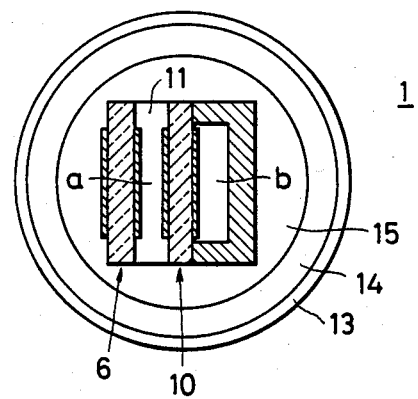
FIG. 2 is a cross section taken along a line I—I of FIG. 1.

FIGS. 1 and 2 show a detector constructed according to a preferred embodiment of the invention. The detector is mounted in an exhaust pipe 1 of an internal combustion engine. The probe 2 of the detector includes a solid electrolyte oxygen pump element 6 and a solid electrolyte oxygen-concentration-difference-actuated electrochemical cell sensor element 10. The pump element 6 consists of an ion-conductive solid electrolyte plate 3 (about 0.5 mm thick and preferably made of stabilized zirconia) having a porous Pt electrode layer 4 formed on one side and another porous Pt electrode layer 5 formed on the other side. Each Pt layer has a thickness of about 20 μm and may be formed by a thick-film deposition technique. The electrochemical cell sensor element 10 also consists of an ion-conductive solid electrolyte plate 7 (about 0.5 mm thick and preferably made of stabilized zirconia) having a porous platinum electrode layer 8 formed on one side and another porous Pt electrode layer 9 formed on the other side.

The pump element 6 and the sensor element 10 are mounted side by side in the exhaust pipe 1 with a gap a therebetween, typically about 0.1 mm or less in width, and are fixed together by filling the gap at the base portion with a heat-resistive and insulating spacer 11. An adhesive filler may be used as the spacer. The edge of the solid electrolyte plate 7 on the side opposite the gap from the pump element 6 is provided with a wall 12 made of a heat-resistive and gas-impermeable material such as a metal or ceramic to form an air compartment b which is open to the atmosphere. This wall 12 is sealed around the porous Pt electrode layer 9, except for its base portion, so that the layer 9 can communicate with the atmosphere.

A support 14 with a male thread 13 is fixed around the base portion of the combined pump element 6, sensor element 10 and wall 12 by means of a heat-resistive and insulating adhesive member 15. The probe 2 is securely mounted in the exhaust pipe 1 by engaging the male thread 13 with a female thread 16 in the exhaust pipe An example of an electronic control unit for use in association with the detector shown above is indicated by reference numeral 17. The porous Pt electrode layer 4 or 5 of the pump element 6 is connected at one end to a switch 18 which changes the direction of oxygen pumping by the pump element 6. The switch 18 has two selectable positions $V_1$ and $V_2$; $V_1$ provides connection to a constant current source $E_1$ connected so as to pump oxygen into the small gap a from the exhaust pipe 1, and $V_2$ provides connection to a constant current source $E_2$ connected so as to pump out oxygen from the small gap a into the exhaust pipe 1. The porous Pt electrode layers 8 and 9 on the electrochemical cell sensor element 10 are connected to output terminals 19 for sensing the electromotive force e generated by the sensor element.

Figure 3:
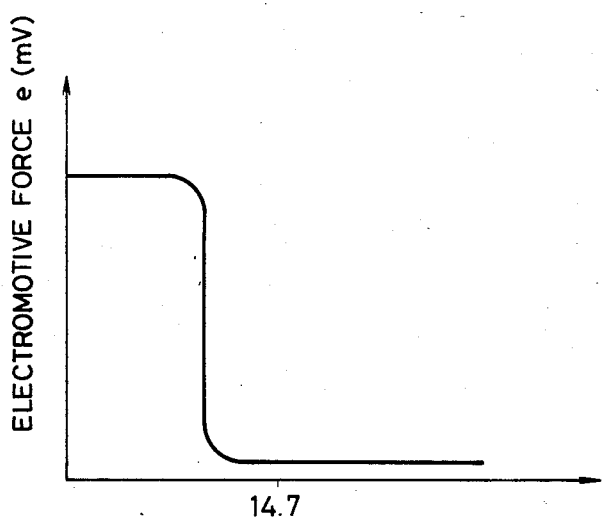
FIG. 3 is a characteristic curve showing the A/F ratio vs. the electromotive force e of the electrochemical cell sensor element of the detector, with the pump-in current (negative value) through the pump element being held constant.

FIG. 3 is a characteristic curve showing the A/F ratio vs. EMF e for the case where the constant current source $E_1$ for pumping oxygen into the small gap a from the exhaust gas in the pipe 1 is held at a negative constant value. In this case, the EMF e drops abruptly in the fuel-rich region where the A/F ratio is less than the theoretical value of 14.7.

Figure 4:
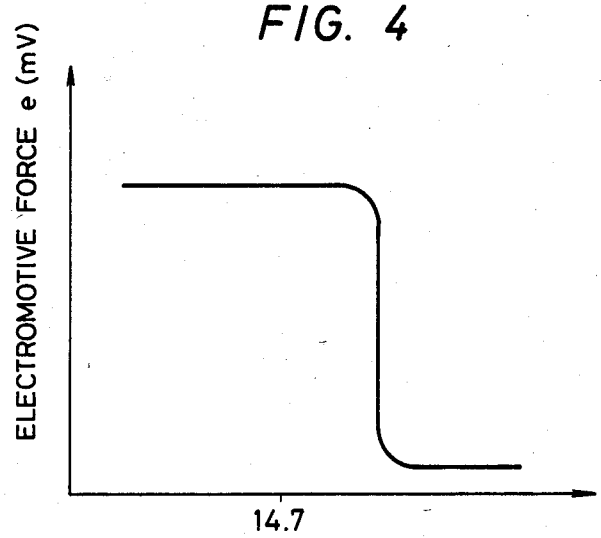
FIG. 4 is a characteristic curve showing the A/F ratio vs. the electromotive force e of the. electrochemical cell sensor element of the detector, with the pump-out current (positive value) being held constant.
Figure 5:
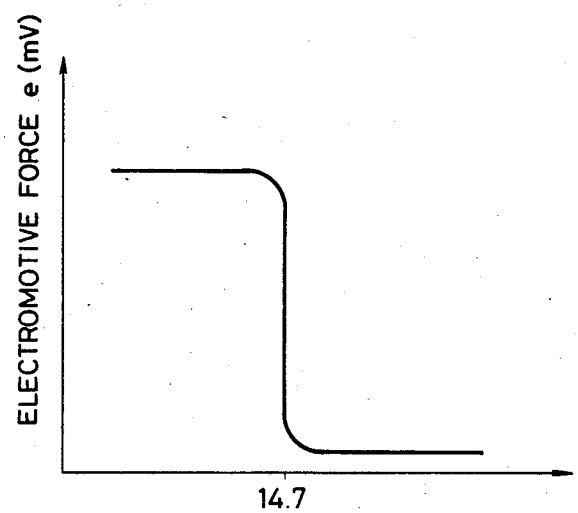
FIG. 5 is a characteristic curve showing the A/F ratio vs. the electromotive force e with no current applied to the pump element.

FIG. 4 is a characteristic curve showing the A/F ratio vs. EMF e for the case where the constant current source $E_2$ for pumping out oxygen from the small gap a into the exhaust pipe 1 is held at a positive constant value. In this case, the EMF e drops abruptly in the fuel-lean region where the A/F ratio is more than the theoretical value of 14.7.

The detector according to this embodiment makes use of the characteristics depicted in FIGS. 3 and 4. When the engine is to be run in the fuel-rich region, the switch 18 is placed at the position $V_1$ for providing at the output terminals 19 the characteristic shown in FIG. 3. By sensing an abrupt change in EMF e in the fuel-rich region, the engine can be controlled to run in the fuel-rich region at A/F ratio values of up to approximately 11. If the engine is to be run in the fuel-lean region, the position $V_2$ is selected for providing at the output terminals 19 the characteristic shown in FIG. 4. By sensing an abrupt change in EMF e in the fuel-lean region, the engine can be controlled to run in the fuel-lean region.

In the embodiment here described, selective control of the A/F ratio in the fuel-rich or fuel-lean region can be achieved by connecting the pump element 6 to either the constant current source $E_1$ of a given negative value (to pump oxygen in) or $E_2$ having a given positive value (to pump oxygen out). The same results can be obtained by other methods. If a large constant current is applied in such a direction that the pump element 6 pumps oxygen into the small gap a from the exhaust gas in the pipe 1, a characteristic wherein the EMF e drops abruptly at a relatively low A/F value in the fuel-rich region is provided at output terminals 19. On the other hand, if a small constant current is applied in the same pump-in direction, a characteristic wherein the EMF e drops abruptly at a relatively high A/F value in the fuel-rich region is provided at the output terminals 19. By utilizing these characteristics in such a manner that the magnitude of the current is continuously or discretely changed to pump oxygen into the small gap a from the exhaust gas in the pipe 1, A/F ratio control or measurement can be performed for all or part of the operating range where the A/F ratio is approximately 11 or higher.

If a small constant current is applied in such a direction that the pump element 6 pumps out oxygen from the small gap a into the exhaust pipe 1, a characteristic wherein the EMF e drops abruptly at a relatively low A/F value in the fuel-lean region is provided at the output terminals 19. If, on the other hand, a large constant current is applied in the same pump-out direction, a characteristic wherein the EMF e drops abruptly at a relatively high A/F value in the fuel-lean region is provided at the output terminals 19. By utilizing these characteristics in such a manner that the magnitude of constant current is continuously or discretely changed to pump out oxygen from the small gap a into the exhaust pipe 1, the A/F ratio control or measurement can be performed for all or part of the fuel-lean region.

If it is desired to run the engine at the theoretical value of 14.7, either the negative- or positive-valued constant current is brought to approximately zero, or instead, the switch 18 is placed in the OFF position so as to discontinue the application of current to the pump element 6. By so doing, a characteristic wherein the EMF e drops abruptly at the theoretical value of 14.7 is obtained at the output terminals 19. The three characteristics shown above may be effectively used to enable precise and quick control or measurement of the operating A/F ratio whether the engine is running in the fuel-rich region, fuel-lean region or at the theoretical value of 14.7.

The characteristics shown above that are provided by the present invention may be used either individually or in combination for the purpose of A/F ratio measurement or A/F ratio feedback control by frequently changing the positions of the switch 18. For detection of A/F values in the fuel-lean region, other techniques may also be used. For example, an electric current can be applied in such a direction that the pump element pumps out oxygen from the small gap a, and the A/F ratio is detected by reading the change in pump current necessary for providing a constant value at the resultant output from the electrochemical cell sensor element.

Figure 6:
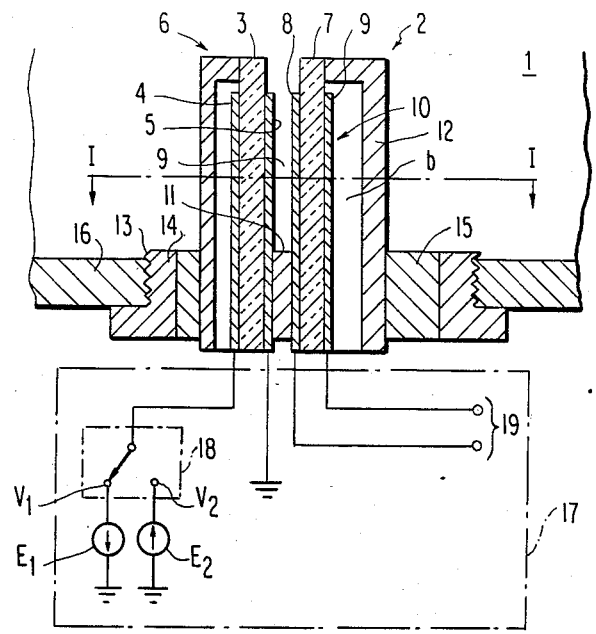
FIG. 6 shows, in cross-section, an air-fuel ratio detector according to a second embodiment of the present invention.
Figure 7:
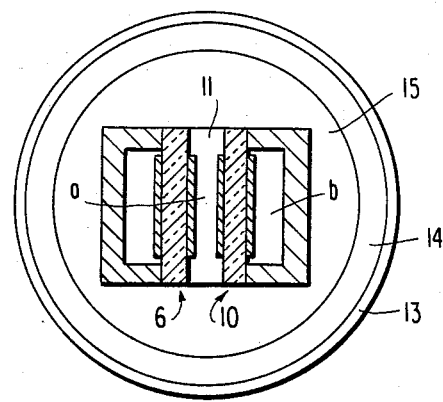
FIG. 7 is a cross-section taken along a line I—I of FIG. 6.

In the above-described embodiment, the electrode layer 4 of the pump element 6 at the opposite electrode layer 5 facing the small gap a is exposed to the exhaust gas to be measured. However, it is possible to provide an air compartment at the side of the electrode layer 4 which is open to the atmosphere, (as shown in FIGS. 6 and 7) similarly to the compartment b of the sensor element 10. As a result, oxygen may be pumped more easily into the small gap a from that air compartment so as to sufficiently measure a A/F ratio in the fuel-rich region.

In the detection probe of the above embodiment of the present invention, the pump element and the sensor element are mounted side by side in the exhaust pipe with a gap therebetween and are fixed together by filling the gap at the base portions with a spacer. It is preferable to sufficiently open peripheral edges of the pump element and the sensor element to the exhaust gases so as to increase the responsivity of the probe. However, the present invention is not limited to the configuration of open edges of the pump element and the sensor element except for their base portions. For example, it is possible to provide support members between the solid electrolyte plates of the pump element and the sensor element for more readily regulating the gap dimensions as far as the support member does not cause any considerable reduction of responsivity. Also, the gap between the pump element and the sensor element is preferably in a range of 0.01 to 0.15 mm. If the gap is too narrow, the responsivity is reduced. The electrode layer which defines the small gap is preferably a porous thick layer having a mean porosity of about 10-40% (as determined by a porosimeter of the pressurized mercury type) in consideration of its diffusion resistance against component gases such as oxygen.

Furthermore, in the case that the electrode layer is formed by a suitable thin-film deposition technique, it is preferable to provide thereon a porous layer such as a ceramic material to which may be added a catalytic agent for obtaining a catalytic action.

A highly responsive detection probe can be readily manufactured using the above-described components.

The characteristics described above that are provided by the detector of the present invention may be used either individually or in combination for the purpose of measurement of feedback control over the operating A/F ratio throughout the dynamic range.

We claim:

1. An A/F ratio detector comprising: a solid-electrolyte oxygen pump element and a solid-electrolyte oxygen-concentration-difference-actuated electrochemical cell sensor element, each element being in the form of an oxygen-ion-conductive solid electrolyte having a porous electrode formed on both sides thereof, said electrochemical cell sensor element being disposed to face said pump element with a small gap therebetween, means for defining an air compartment open to the atmosphere on a side of said sensor element opposite said small gap, and means for passing an electric current through said pump element, a resulting output from said sensor element providing an output signal indicative of an air/fuel ratio.

2. The A/F ratio detector of claim 1, wherein said means for defining an air compartment comprises a wall extending parallel to said solid electrolyte of said sensor element.

3. The A/F ratio detector of claim 2, wherein said wall is made of a heat-resistive and gas-impermeable material.

4. The A/F ratio detector of claim 3, wherein said material of said wall is a metal.

5. The A/F ratio detector of claim 4, wherein said material of said wall is a ceramic.

6. The A/F ratio detector of claim 2, wherein said wall is sealed to said solid electrolyte of said sensor element around a peripheral portion of said wall except at a base portion of said wall.

7. The A/F ratio detector of claim 1, wherein said means for passing an electric current through said pump element comprises switchable current source means for selectively establishing a direction of current flow through said pump element.

8. The A/F ratio detector of claim 1, wherein said means for passing an electric current through said pump element comprises first and second current sources and switch means for selectively connecting one of said first and second current sources to said pump element, said first and second current sources being connected to provide current flows in opposite directions through said pump element.

9. The A/F ratio detector of claim 1, wherein said means for passing an electric current through said pump element comprises first and second current sources for supplying currents of different magnitudes, and switch means for selectively connecting one of said first and second current sources to said pump element.

10. An A/F ratio detector comprising: a solid-electrolyte oxygen pump element and a solid-electrolyte oxygen-concentration-difference-actuated electrochemical cell sensor element, each element being in the form of an oxygen-ion-conductive solid electrolyte having a porous electrode formed on both sides thereof, said electrochemical cell sensor element being disposed to face said pump element with a small gap therebetween, means for defining an air compartment open to the atmosphere on a side of said sensor element opposite said small gap, means for passing an electric current through said pump element, means for defining an air compartment open to the atmosphere on a side of said pump element opposite said small gap, and a resulting output from said sensor element providing an output signal indicative of an air/fuel ratio.

11. The A/F ratio detector of claim 10, wherein said means for defining an air compartment comprises a wall extending parallel to said solid electrolyte of said pump element.

12. The A/F ratio detector of claim 11, wherein said wall is made of a heat-resistive and gas-impermeable material.

13. The A/F ratio detector of claim 12, wherein said material of said wall is a metal.

14. The A/F ratio detector of claim 13, wherein said material of said wall is a ceramic.

15. The A/F ratio detector of claim 11, wherein said wall is sealed to said solid electrolyte of said pump element around a peripheral portion of said wall except at a base portion of said wall.

* * * * *

UNITED STATES PATENT AND TRADEMARK OFFICE
CERTIFICATE OF CORRECTION

PATENT NO. : 4,591,421

DATED : May 27, 1986

INVENTOR(S) : Tetsusyo Yamada and Shintaro Hirate

It is certified that error appears in the above-identified patent and that said Letters Patent is hereby corrected as shown below:

Item [73] should read as follows:

-- ASSIGNEES: NGK Spark Plug Co., Ltd and

Mitsubishi Denki Kabushiki Kaisha --.

Signed and Sealed this

Twenty-third Day of September 1986

[SEAL]

*Attest:*

DONALD J. QUIGG

*Attesting Officer*     *Commissioner of Patents and Trademarks*